US012751607B2

(12) United States Patent
Buschle et al.

(10) Patent No.: US 12,751,607 B2
(45) Date of Patent: Oct. 6, 2026

(54) MEDICAL IMAGING DEVICE AND METHOD FOR CALIBRATING A MEDICAL IMAGING DEVICE

(71) Applicant: KARL STORZ SE & Co. KG, Tuttlingen (DE)

(72) Inventors: Lukas Buschle, Tuttlingen (DE); Werner Göbel, Tuttlingen (DE); Hannes Köhler, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 47 days.

(21) Appl. No.: 18/710,774

(22) PCT Filed: Nov. 22, 2022

(86) PCT No.: PCT/EP2022/082723
§ 371 (c)(1),
(2) Date: May 16, 2024

(87) PCT Pub. No.: WO2023/094351
PCT Pub. Date: Jun. 1, 2023

(65) Prior Publication Data

US 2025/0040795 A1 Feb. 6, 2025

(30) Foreign Application Priority Data

Nov. 24, 2021 (DE) ..................... 10 2021 130 790.2

(51) Int. Cl.
*A61B 1/06* (2006.01)
*A61B 1/00* (2006.01)

(52) U.S. Cl.
CPC ............ *A61B 1/06* (2013.01); *A61B 1/00013* (2013.01)

(58) Field of Classification Search
CPC ... A61B 1/06; A61B 1/00013; A61B 1/00009; A61B 1/00006; A61B 1/00057;
(Continued)

(56) References Cited

U.S. PATENT DOCUMENTS

2005/0194876 A1 9/2005 Shimada et al.
2012/0075447 A1 3/2012 Iwane
(Continued)

FOREIGN PATENT DOCUMENTS

DE 102019134473 A1 6/2021
DE 102020105458 A1 6/2021
(Continued)

OTHER PUBLICATIONS

International Search Report for International Application No. PCT/EP2022/082723, mailed Feb. 27, 2023.
(Continued)

*Primary Examiner* — Nasim N Nirjhar
(74) *Attorney, Agent, or Firm* — Jason H. Vick; Amped IP LLC

(57) ABSTRACT

The invention relates to a medical imaging device, in particular a laparoscope, endoscope and/or exoscope, having a light source for illuminating a viewing area, a lens having an optical path for capturing the viewing area and imaging first image information of the viewing area on an image capturing device, having a sensitivity distribution such that the first image information is captured by the image capturing device and imaging second image information of said viewing area on said image capturing device such that said second image information is captured by said image capturing device, and an adjustment device for adjusting image
(Continued)

Figure 1:
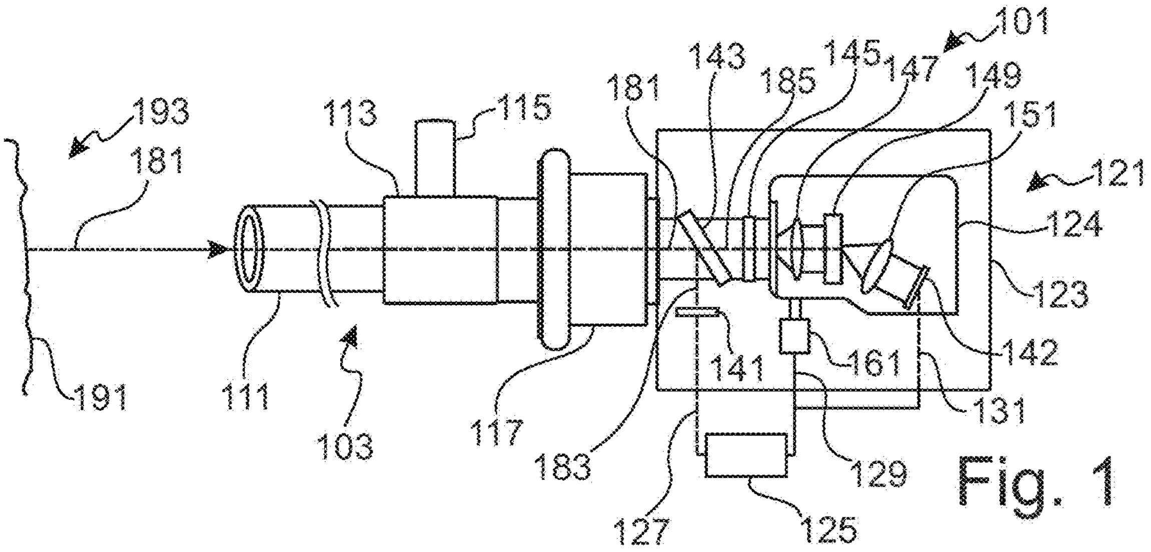

parameters of the image capturing device, wherein the adjustment device is associated with a control unit, wherein the first image information can be captured by the control unit and the control unit controls the adjustment device in dependence on the first image information for adjusting the sensitivity distribution with a calibration correlation between the first image information and the second image information so that, by means of the adjustment device, there is calibration of the second image information, dependent on the first image information, for the image capturing device.

18 Claims, 4 Drawing Sheets

(58) Field of Classification Search
CPC ............ A61B 1/00172; G02B 23/2484; H04N 25/61; H04N 23/555

See application file for complete search history.

(56) References Cited

U.S. PATENT DOCUMENTS

| | | | | |
|---|---|---|---|---|
| 2017/0319053 | A1* | 11/2017 | Kamee | A61B 1/0661 |
| 2022/0210309 | A1* | 6/2022 | Feingold | A61B 1/00009 |
| 2023/0029348 | A1 | 1/2023 | Bauer et al. | |

FOREIGN PATENT DOCUMENTS

| | | | | |
|---|---|---|---|---|
| EP | 2851662 | A2 * | 3/2015 | G01J 3/2823 |
| JP | 5827720 | B2 | 12/2015 | |
| WO | 2020257027 | A1 | 12/2020 | |

OTHER PUBLICATIONS

Written Opinion for International Application No. PCT/EP2022/082723, mailed Feb. 27, 2023.
German Office Action, Application No. 10 2021 130 790.2, 2022-08-19, pp. 1-9, Munich, Germany.
Office Action for corresponding European Application No. 22821894.7, mailed Aug. 19, 2026.

* cited by examiner

MEDICAL IMAGING DEVICE AND METHOD FOR CALIBRATING A MEDICAL IMAGING DEVICE

CROSS REFERENCE TO RELATED APPLICATIONS

This application is a national stage application under 35 U.S.C. 371 of PCT Application No. PCT/EP2022/082723 having an international filing date of 22 Nov. 2022, which designated the United States, which PCT application claimed the benefit of German Application No. 10 2021 130 790.2, filed 24 Nov. 2021, each of which are incorporated herein by reference in their entirety.

The invention relates to a medical imaging device, in particular a laparoscope, an endoscope and/or an exoscope, having a light source for illuminating a viewing area, a lens having an optical path for capturing a viewing area and imaging first image information of the viewing area on an image capturing device, having a sensitivity distribution such that the first image information is captured by the image capturing device and imaging second image information of the viewing area on the image capturing device such that the second image information is captured by the image capturing device, and an adjustment device for adjusting image parameters of the image capturing device. The invention further relates to a method for calibrating a medical imaging device according to the type described above.

In known imaging devices, in particular in medical imaging devices, an image sensor, for example, which acts as an image capturing device, is calibrated as part of a factory setting or a presetting. In this case, in particular if the image capturing device has different sensor fields or different sensor areas, it is often not possible to carry out a calibration that is appropriate for the purpose.

In this context, for example, medical imaging devices with so-called hyperspectral imaging are also known, with hyperspectral imaging, for example, being used to scan a viewing area line by line and corresponding spectral information can be read out from this viewing area. Such medical imaging devices, for example endoscopes, with hyperspectral imaging must be calibrated at the factory, which results in different problems, for example in connection with a signal-to-noise ratio, depending on the exposure state of the viewing area. For example, very strong noise can occur compared to a useful signal, for example dependent on the respective exposure, and the useful signal can therefore be falsified.

The object of the invention is to improve the prior art.

The object is achieved by a medical imaging device, in particular a laparoscope, an endoscope and/or an exoscope, having a light source for illuminating a viewing area, a lens having an optical path for capturing the viewing area and imaging first image information of the viewing area on an image capturing device, having a sensitivity distribution such that the first image information is captured by the image capturing device and imaging second image information of said viewing area on said image capturing device such that said second image information is captured by said image capturing device, and an adjustment device for adjusting image parameters of the image capturing device, with the adjustment device being associated with a control unit, with the first image information being able to be captured by the control unit and the control unit controlling the adjustment device in dependence on the first image information for adjusting the sensitivity distribution with a calibration correlation between the first image information and the second image information so that, by means of the adjustment device, there is calibration of the second image information, dependent on the first image information, for the image capturing device.

Thus, the first image information can be used, for example, as a reference such that the sensitivity distribution of the image capturing device is adjusted in dependence on the first image information in such manner that the second image information with a sensitivity distribution adjusted in this way is read out and further used, for example. Consequently, there is calibration of the second image information for the image capturing device, dependent on the first image information, and thus, for example, the second image information can be captured in such manner that an intensity range of the image capturing device, in which a particularly low-noise capturing of image information is possible, is optimally utilised or else the image capturing device is effectively prevented from correspondingly exceeding a corresponding capture capacity.

The following terms are explained in this context:

A "medical imaging device" can be any technical and/or electronic device that is suitable for capturing, further processing and/or forwarding an image of a viewing area in a medical environment and, for example, displaying it on a screen. For example, such a medical imaging device is an endoscope, a dual endoscope, a stereo endoscope, an exoscope or a stereo exoscope. Such an "endoscope" here is a usually narrow and elongated imaging device, which is suitable for being inserted into a cavity or through a usually small opening and capturing an image of a viewing area within the cavity and/or the area behind the small opening, in the case of a "stereo endoscope" using two cameras or two image sensors. An "exoscope" is a comparable device that is used, for example, for external imaging during medical procedures, i.e. in a so-called open surgical procedure. The "stereo" property of the respective endoscope or exoscope in this case describes the ability to capture a stereoscopic image of the viewing area using two optical paths and/or two lenses. A corresponding dual endoscope or dual exoscope is able to capture two separate images without, for example, a stereoscopic reconstruction. In this context, it should be noted that a respective "endoscope" in the actual sense, as described above, can also be integrated within an endoscope system with further devices, for example a cable guide, further sensors and/or a display device for displaying image information on an external monitor. Furthermore, "endoscope" and "endoscope systems" are often not clearly distinguished and are used synonymously here.

A "laparoscope" is in particular in this case a medical imaging device which is used for so-called laparoscopy, i.e. an examination of the abdomen, in particular the abdominal cavity. This is a type of endoscope in which a particularly rigid shaft of the laparoscope can be inserted into an abdominal cavity using a guiding aid called a "trocar". Such a laparoscope comprises, for example, a small camera at one end which is inserted into the abdominal cavity and which can also be referred to as an endoscope. Furthermore, a laparoscope also comprises optical lens systems, i.e. a lens that is used, for example, for magnification. Basically, the optical mode of operation of such a laparoscope is thereby comparable to the optical mode of operation of an endoscope or an exoscope.

A "light source" is, for example, an LED, an incandescent lamp or another light-emitting device. Furthermore, such a light source can also be implemented in that a light generated by an LED or another light-generating device is directed or guided to a corresponding location in the viewing area by means of, for example, a light guide, for example a glass fibre or a glass fibre bundle. Such a light source thereby serves to illuminate the viewing area with light of corresponding light spectra.

A "viewing area" describes the area, volume or site that is to be viewed using the medical imaging device and of which a corresponding image is to be generated. Such a viewing area is thereby, for example, an organ, a bone, a partial area of a human or animal body or another area of interest for a corresponding observation.

"Illuminating" the viewing area here describes the introduction of light into the viewing area, for example the irradiation of light of different wavelength ranges into the viewing area. A "lens" describes the entirety of all components that direct light and/or image information or an image along the optical path. For example, such a lens here includes lenses, cover panes, protective panes or even filters.

An "optical path" is in particular the path through which light of a corresponding image or corresponding image information travels from the viewing area via a respective lens to, for example, the image capturing device or to a respective image sensor. Such an optical path is defined here, for example, by means of an optical axis or as a geometric course.

"Capturing the viewing area" describes guiding, directing and/or channelling image information or light information of the viewing area, for example an image of the viewing area, via the optical path of the lens such that imaging of corresponding image information is possible.

"Imaging" corresponding image information describes the generation of an image point from an object point by combining and/or deflecting light that emanates from the object point, with this imaging process being carried out for different, i.e. a plurality of image points. Such imaging is thereby done using a lens.

"Image information" of the viewing area here is corresponding optically and/or electronically processed information, which results from imaging the viewing area and which can be further processed, for example, in an electronic device. For example, this is a data format that represents an image of the viewing area. Before the viewing area is imaged on an image capturing device, this image information also comprises the optical properties, for example the light, which is imaged on the image capturing device. The transition from physical image information, i.e. the properties of light, to digital image information, for example, is fluid in this case.

An "image capturing device" is, for example, an electronic chip or another similar device by means of which light running along the optical path and the respective lens and/or corresponding image information can be captured and, for example, converted into electronic signals. For example, such an image capturing device has components of a CCD chip or a comparable electronic component, with the image capturing device being able to have, for example, different areas, different sections or different components which can capture different image information.

A "sensitivity distribution" describes varying sensitivity of the image capturing device to incident light according to an extension of the image capturing device, in particular in different axes, such that, for example, edge areas of the image capturing device are less sensitive than a central area or a different sensitivity distribution is present, which has an influence on the respective image information and/or on the intensity and/or quality of the image information.

An "adjustment device" can be an optical, an electronic and/or a mechanical device which is suitable for adjusting image parameters of the image capturing device and thus changing and/or influencing a capture behaviour of the image capturing device, for example in relation to the sensitivity distribution. Such an adjustment device can here, for example, enable an aperture adjustment, an exposure adjustment or an adjustment for a specific type of directing and/or guiding of light.

An "image parameter" thereby represents a property of corresponding image information, in particular image information captured by the image capturing device, which can be influenced. Such an image parameter can thereby in particular also be fixed or changed pixel by pixel, i.e. for a few image points or for each image point of the image capturing device. In particular, such an image parameter is an exposure setting, an exposure time and/or an alignment of the image capturing device relative to, for example, the viewing area and/or relative to, for example, the lens.

In this case, a "control unit" is used, which is, for example, a computer, a microprocessor or another type of device, for example also a mechanical device, by means of which it is possible to influence the adjustment device in such manner that a desired effect on the adjustment device is achieved. For example, such a control unit can be a computer which captures corresponding signals, processes them according to a stored algorithm and then exerts a targeted influence on the adjustment device such that corresponding settings are made by means of the adjustment device using the control unit.

The control unit thereby controls the adjustment device in dependence on the first image information in such manner that the first image information is captured and, for example, evaluated such that the sensitivity distribution can then be adjusted with a calibration correlation between the first image information and the second image information. For example, the sensitivity distribution is calculated or overlaid with a calibration correlation such that the sensitivity distribution is adjusted based on the calibration correlation and thus, for example, the image capturing device is adjusted in such manner that a signal-to-noise ratio is advantageously achieved and/or a corresponding exposure is optimised.

A "calibration" here describes the process in which the sensitivity distribution is overlaid with the calibration correlation, for example, and thus there is a calibrated sensitivity distribution. Calibration is thereby the process that detects a deviation from an ideal and, in a second step, corrects it to a so-called "normal", with corresponding deviations ideally being completely or at least largely eliminated by the calibration.

In order to be able to construct the medical imaging device according to the invention as simply as possible and with few components, the adjustment device can be introduced into the optical path by means of a switching device such that the first image information can be captured by the control unit in a first switching state of the switching device, in which the adjustment device is not introduced in the optical path, and the control unit controls the adjustment device in a second switching state of the switching device in dependence on the first image information for adjusting the sensitivity distribution with a calibration correlation between the first image information and the second image information, with the image capturing device in particular having a first image sensor for capturing the first image information and the second image information.

Thus, a first image sensor, which is used alone, can be connected by means of the switching device in such manner that the function according to the invention is fulfilled with only one first image sensor.

A "switching device" is here, for example, a device for optically or mechanically switching corresponding switching states, and in the case of optical switching, for example by means of corresponding mirrors, lenses or other optical components, the optical path is in particular redirected around the adjustment device such that, in a first switching state, the optical path runs around the adjustment device and, in a second switching state, the optical path runs in such manner that the adjustment device is in engagement with the optical path. Alternatively, the adjustment device can also be pivoted into the optical path or introduced in some other way such that, in the first switching state, the adjustment device is not introduced mechanically in the course of the optical path and, in the second switching state, it is introduced in the direct optical path.

Alternatively or in addition to this, the optical path has a first optical partial path for imaging the first image information on the image capturing device and a second optical partial path for imaging the second image information on the image capturing device, with the first image information being able to be captured by the control unit in the first optical partial path and the control unit controlling the adjustment device in the second optical partial path in dependence on the first image information for adjusting the sensitivity distribution with a calibration correlation between the first image information and the second image information, with the image capturing device in particular having a first image sensor associated with the first optical partial path with a first sensitivity distribution for capturing the first image information and a second image sensor associated with the second optical partial path with a second sensitivity distribution for capturing the second image information.

Thus, in particular, respective image information can be captured simultaneously by means of the first image sensor and the second image sensor such that in particular the calibration correlation is also formed and/or applied in real time such that at best a simultaneous capturing of the first image information and the second image information can take place with a calibration of the second image information.

An "optical partial path" is here a corresponding section and/or a corresponding optical path running parallel or separately from another partial path such that the optical path is in particular divided into a plurality of optical partial paths and corresponding image information is guided along a respective optical partial path and therefore can be imaged separated from one another in particular on different image sensors.

"Real time" here describes the execution of technical or electronic processes in such manner that reliable processing, display and/or representation of the processes takes place within a specified time. In the narrower sense, the term "real time" is also used in such manner that, for example, an operator has the impression of the simultaneity of events, i.e. the feeling of a "real-time" representation, for example, based on the operator's real impression of time. For example, a representation takes place in parallel with a frame rate of more than 24 frames per second or even a higher frame rate, such that an operator can no longer distinguish between individual frames.

In order, for example, to be able to reliably carry out a factory calibration or a calibration before a respective use of the respective medical imaging device, the calibration correlation is formed based on reference image information, in particular based on different reference image information with, in particular, respective exposure settings.

Such "reference image information" is here, for example, an image panel of a specific, uniform colour, such as for example a white panel or a grey panel, based on which a known colour distribution, in particular a known uniform colour distribution, for example an exposure or other information relating to the calibration correlation, can be reliably recognised and the calibration correlation can be formed therefrom.

An "exposure setting" is a specific setting by means of which a corresponding light sensitivity of the image capturing device, in particular an image sensor, is taken into account and adjusted.

In this context, an "image sensor" can be, for example, an electronic chip or another similar device by means of which light and the respective lens and/or a corresponding image running along the optical path can be recorded and converted into electronic signals. For example, such an image sensor is a CCD chip or a comparable electronic component.

In one embodiment, the calibration correlation is formed based on a white balance and/or based on a black balance or based on a plurality of white balances and/or based on a plurality of black balances, in particular in dependence on an exposure setting or dependent on a plurality of exposure settings of the second image sensor.

In this way, for example in connection with corresponding reference image information, a reliable and comprehensible and therefore reproducible comparison and such formation of the calibration correlation can be ensured.

A "white balance" serves to adjust corresponding image information, for example photographic information, in such manner that effects caused by, for example, different light wavelengths of the light source at a capture location, for example at the viewing area, are taken into account and thus, for example, discolouration of corresponding image information is prevented or compensated for in the best possible way. In this context, adjusting the colour temperature is also spoken about. In contrast, with a "black balance", a setting takes place in such manner that it is ensured that black image parts or black components of the image information, in particular from an electronic camera, such as for example an electronic image sensor, are also reproduced in black and do not have any colour distortion. For example, an aperture is thereby completely closed such that no more light falls on a corresponding image sensor. Corresponding individual signals from, for example, colour channels of an image sensor are then compared such that a corresponding image signal is output.

In order to be able to maintain a corresponding calibration correlation for the use of the medical imaging device as a preventative measure, the calibration correlation is available for different illumination intensities, in particular different illumination intensities of the light source.

Thus, for example, a corresponding calibration correlation can be stored for fixedly set illumination types, for example corresponding illumination intensities of the light source, for example as part of a factory setting for the medical imaging device, such that, for example, when adjusting the light source or switching the light source to a differently coloured illumination type or a different illumination intensity, the respective one calibration correlation is at least basically already available. In addition, a further calibration correlation can then also be determined by correspondingly evaluating the first image information, for example for a readjustment of the factory setting.

In a further embodiment, the adjustment device has a frame manipulator, with a frame rate of the image capturing device, in particular of the second image sensor, and/or a frame count of the image capturing device, in particular of the second image sensor, being able to be adjusted by means of the frame manipulator and/or having an exposure manipulator, with an exposure intensity and/or an exposure duration of the image capturing device, in particular of the second image sensor, being able to be adjusted by means of the exposure manipulator.

By means of such a frame manipulator, for example by adjusting the frame rate of the image capturing device, in particular of the second image sensor, an adjusted and fastest possible capturing of corresponding image information can take place, namely, for example, by increasing the frame rate if it can be read from the first image information that the exposure intensity of the second image sensor is sufficient and the frame rate can therefore be increased accordingly without having to accept any loss in quality of the second image information.

In contrast or in addition, a corresponding frame count of the image capturing device, in particular of the second image sensor, can be adjusted to a corresponding calibration correlation or corresponding information of the first image sensor or the first image information such that an exposure intensity and/or an exposure duration of the image capturing device, in particular of the second image sensor, can be adjusted based on this data, for example, to optimise a capture speed, avoidance of movement artefacts or other effects.

In order to be able to use the medical imaging device in particular to determine physiological parameters of the viewing area, the image capturing device has a spectral sensor, in particular a hyperspectral sensor with a line-by-line scanning of image information of the viewing area, with the hyperspectral sensor in particular having a slit aperture and/or a grating aperture for in particular variable interruption and/or deflection of the respective image information.

In the present case, “physiological parameters” of the viewing area are, for example, an oxygen concentration, corresponding fat proportions, blood flow values, a haemoglobin concentration or also a water proportion in, for example, an organ being viewed and/or the tissue of the respective organ being viewed in the viewing area. Such physiological parameters can be determined, for example, by means of corresponding light spectra by analysing an absorption level for a wavelength or a corresponding wavelength range or even a plurality of absorption levels for a plurality of wavelength ranges of a light spectrum and drawing conclusions about a corresponding physiological parameter. For example, a specific absorption wavelength or a plurality of absorption wavelengths or certain absorption wavelength ranges is associated with a haemoglobin concentration, another absorption wavelength or a plurality of such absorption wavelengths or absorption wavelength ranges is associated with a water content or a third absorption wavelength or a plurality of absorption wavelengths or absorption wavelength ranges is associated with an oxygen content in the blood. Corresponding wavelength ranges for determining different physiological parameters here can be the same, overlapping or different or can be used in different combinations.

A “spectral sensor” is a sensor, for example an image sensor or another light-sensitive sensor, which is able to capture spectral information, for example image information, and thus output information about, for example, a spectral distribution in the viewing area, such that, for example, physiological parameters can be determined based on the spectral distribution.

In this context, a “hyperspectral sensor” has, for example, a spectrometer unit that splits incident light depending on the wavelength through a so-called observation gap and through a prism or an optical grating. Correspondingly split light is then fed to an image sensor of the hyperspectral sensor and detected by it. Individual recordings from a hyperspectral sensor thus provide spectral information for a so-called image line of an object, for example an image line from the viewing area. By moving, for example, the observation gap, an object, for example an object in the viewing area, can then be completely swept over line by line, such that a so-called hyperspectral data cube is created over a total area from the viewing area, i.e. multidimensional information which, for example, for each pixel, i.e. each image point, provides an optical spectrum in the image, for example a distribution of light wavelengths. Thus, for example, a distribution of light wavelengths in the range from 500 nm to 1,000 nm over a complete area of the viewing area can be reliably determined for each image point individually. For example, physiological tissue parameters can then be derived and/or calculated from such a hyperspectral data cube.

A “slit aperture” is here, for example, the mechanical means by which such an observation gap is created. For example, this is a metal sheet with a corresponding slit. A “grating aperture” is here, for example, a corresponding sequence of slits in the form of similarly or identically designed slits in an aperture. This means that image information can then be variably interrupted or even directed or diffracted.

In order to design the medical imaging device to be structurally simple, the adjustment device has a motor, in particular an adjustment motor, with the slit aperture and/or the grating aperture being able to be moved by means of the motor and/or by means of the adjustment motor, such that the variable interruption and/or deflection of the respective image information is carried out by moving the slit aperture and/or grating aperture.

A “motor” is here a mechanical device, for example an electromechanical device, which converts the energy provided into, for example, a rotation or translation, i.e. into a physical movement. For example, an electric motor, a hydraulic motor, a magnetic motor or another type of motor can be used here.

In a further embodiment, the control unit is associated with a calculation unit for calculating a predicted capture duration of the respective image information based on the calibration correlation and/or based on operating parameters of the control unit, the image capturing device, the first image sensor and/or the second image sensor.

This allows a predicted capture duration to be calculated, for example from past image information of a first image sensor, and/or from the previous course of a corresponding capture and a sweep of the viewing area to generate the hyperspectral data cube, such that, for example, a corresponding capture duration can be displayed to an operator up to which a corresponding medical imaging device, for example, may not be moved.

A “calculation unit” is here, for example, a computer chip or a computer or a corresponding algorithm on a computer for operating the medical imaging device, which can carry out a corresponding calculation based on a stored algorithm.

“Operating parameters” of the control unit are here, for example, physical properties of the control unit, corresponding properties set by an operator or, for example, an exposure setting of the control unit, the image capturing device, the first image sensor and/or the second image sensor.

In a further embodiment, the image capturing device has a sensor for capturing an image visible to an operator, in particular an RGB image, and/or the first image sensor is an image sensor for capturing an image visible to an operator, in particular an RGB sensor and/or a white light sensor.

By means of such an RGB sensor or a sensor for capturing a corresponding image, a visible image of the viewing area can also be represented for the operator in parallel with the generation of the spectral image information or, for example, in parallel or alternately at intervals to capture physiological parameters.

An "RGB image" is here an image that is in particular visible to an operator and consists of corresponding colour information, namely red, green and blue colour information, which is then put together to form a visible image with different colour representations.

An RGB sensor is in particular an electronic sensor, which, for example, has corresponding filters in front of it, such that certain sensor areas can only receive light information of a certain colour, thus enabling separation according to different colours. In general, such an RGB sensor is also called a "white light sensor" because such a sensor can capture light from various colour spectra. Such an RGB sensor is usually designed as a sensor with a so-called Bayer filter.

In a further aspect, the object is achieved by a method for calibrating a medical imaging device according to one of the previously described embodiments, having the following steps:

- capturing the first image information with the image capturing device such that the first image information is present in the image capturing device,
- controlling the adjustment device by means of the control unit by adjusting the second sensitivity distribution with the calibration correlation such that calibrated second image information is present,
- such that a calibration of the second image sensor is achieved.
- By means of such a method, it is easily possible to carry out a calibration of the second image sensor based on image information of the first image sensor and thus to operate the second image sensor such that high-quality capturing is possible.

"Calibrating" here describes the activity that brings about a calibration. Calibration can therefore here comprise capturing information and comparing the information with a desired standard or a desired normal; it can also be part of the calibration to carry out a corresponding sequence, such as controlling the adjustment device, based on this information.

In one embodiment, the control is carried out based on partial information of the first image information, in particular based on an average pixel intensity of the first image information, based on a maximum pixel intensity of the first image information and/or based on a pixel intensity distribution of the first image information.

With this method, in particular, a uniform calibration or a targeted calibration can be carried out based on the corresponding partial information, i.e. based on a specific significant feature of the image information.

In this context, "partial information" can be any image information that describes, depicts or represents a specific feature, quality or property of the image information in its entirety or in part. For example, such partial information is designed as an average pixel intensity, maximum pixel intensity and/or pixel intensity distribution of the first image information. A "pixel intensity" here describes, for example, a luminosity of a pixel or, analogously, signal strength with respect to a corresponding pixel, i.e. with respect to an image point or a partial area of the image or the image information, with the calibration then being carried out based on, for example, the average pixel intensity, i.e. an average intensity distribution of corresponding pixels. The calibration can also be carried out based on a maximum pixel intensity such that, for example, overdriving an image sensor is effectively prevented. Analogously, a pixel intensity distribution, i.e. the distribution of corresponding signal strengths, can be used to take smoothing of corresponding image information components into account in the calibration.

In order to carry out a reliable and timely calibration, particularly in connection with the hyperspectral image capturing, the control of the second image sensor is carried out line by line such that the calibration is carried out line by line for a respective line.

Thus, for example, a respective calibration can be carried out for a line of hyperspectral image capturing in such manner that, if the viewing area is unevenly illuminated, a respective line is adjusted, for example based on its exposure, such that a signal-to-noise ratio is set as favourably as possible, i.e. that a corresponding line is optimally exposed. Thus, if, for example, an exposure time is used as a setting value to control the adjustment device, a total capture time can be optimised in such manner that the shortest possible exposure time determined based on the calibration is used, ensuring in each case that the exposure time is sufficient to represent an optimally illuminated line.

In a further embodiment, a control measurement with a comparison of the sensitivity distribution, the calibration correlation, the first sensitivity distribution and/or the second sensitivity distribution is carried out by means of a control unit associated with the adjustment device in order to check the accuracy of the calibration.

By means of such a control unit, a closed control loop can be set up, by means of which a corresponding calibration can be controlled during operation or at intervals between corresponding operating states.

A "control unit" is here, for example, a computer or a computer chip, in particular a computer or a computer chip with a corresponding algorithm, which has, for example, reference values or corresponding control values, which are then used as part of a comparison to check the accuracy of the calibration.

A "control measurement" here describes the process in which a corresponding check of the accuracy is carried out, for example at the time the control measurement is triggered by an operator and/or automatically, for example as part of a closed control loop.

In order to ensure reliable calibration, particularly when using different image formats and/or when transmitting different bandwidths for different image formats, the calibration correlation is converted based on a ratio of a first image size of the first image information and a second image size of the second image information, in particular based on a respective length and/or based on a respective width of the respective image information, such that a size-adjusted, format-adjusted, length-adjusted and/or width-adjusted overlay of the calibration correlation with the respective sensitivity distribution is possible.

A "ratio" of a first image size to a second image size here describes, for example, a factor for converting corresponding pixel ratios, corresponding length ratios or corresponding width ratios, with a respective "length" and a respective "width" here representing any dimension of such an image size. The width of an image in the horizontal direction and the length of an image in the vertical direction are usually specified here. The "length" of an image can also be described here as "height".

In a further embodiment, the calibration is carried out during the capture of the first image information by means of an ongoing calibration and/or after the capture of the first image information by means of a subsequent calibration, in particular in real time, in particular in an evaluation unit.

In this way, a calibration can be carried out either directly during the capture or in a sequence that is in particular not perceivable by an operator in time.

In order to ensure trouble-free operation of the medical imaging device, the illumination intensity of the light source is adjusted, in particular in dependence on the calibration correlation.

Thus, for example, if it is determined during the calibration that an illumination intensity is not sufficient for a sufficiently high-quality image, in particular a hyperspectral recording, the illumination intensity of the light source can be corrected or adjusted accordingly. In particular, this takes place in dependence on the calibration correlation such that, for example, corresponding limit values are stored within the control unit and/or the adjustment device or a further component, and if this is exceeded or undercut, the illumination intensity of the light source is correspondingly corrected. This adjustment of the illumination intensity of the light source can take place frame by frame or line by line, such that, for example, by adjusting the illumination intensity of the light source, the capture duration can be optimised in time, for example by increasing the illumination intensity, a corresponding exposure is made possible, which allows a shorter exposure time.

Figure 2:
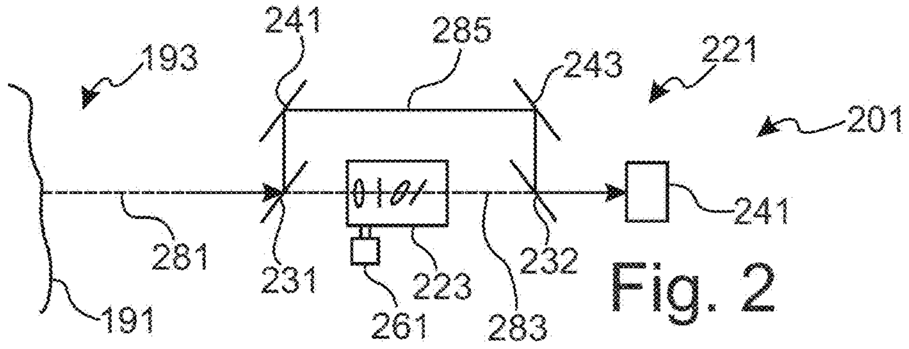
Figure 3:
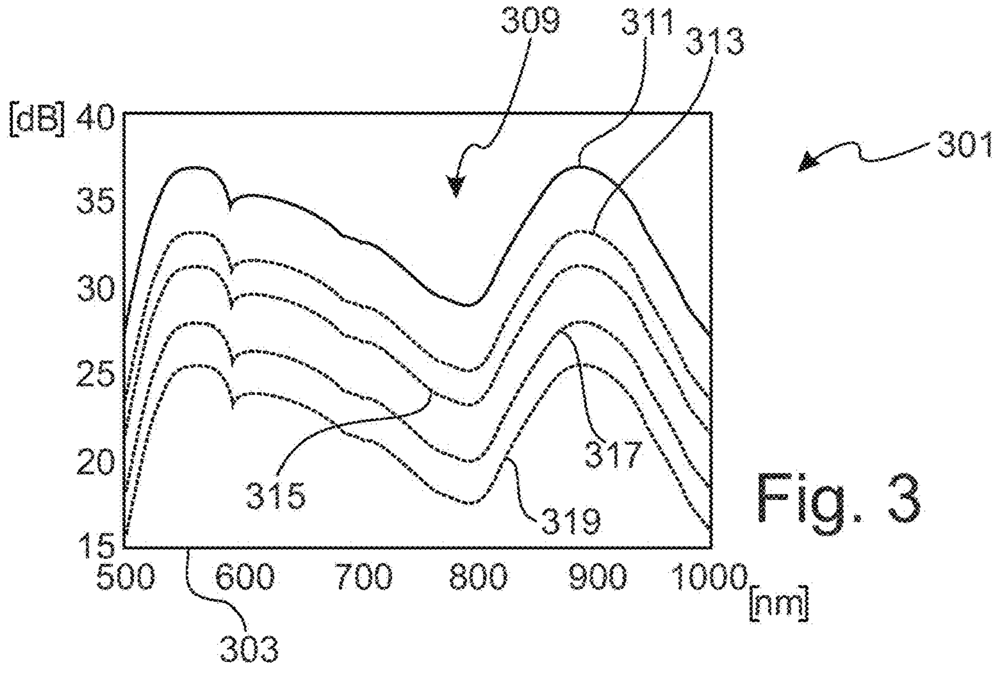
Figure 4:
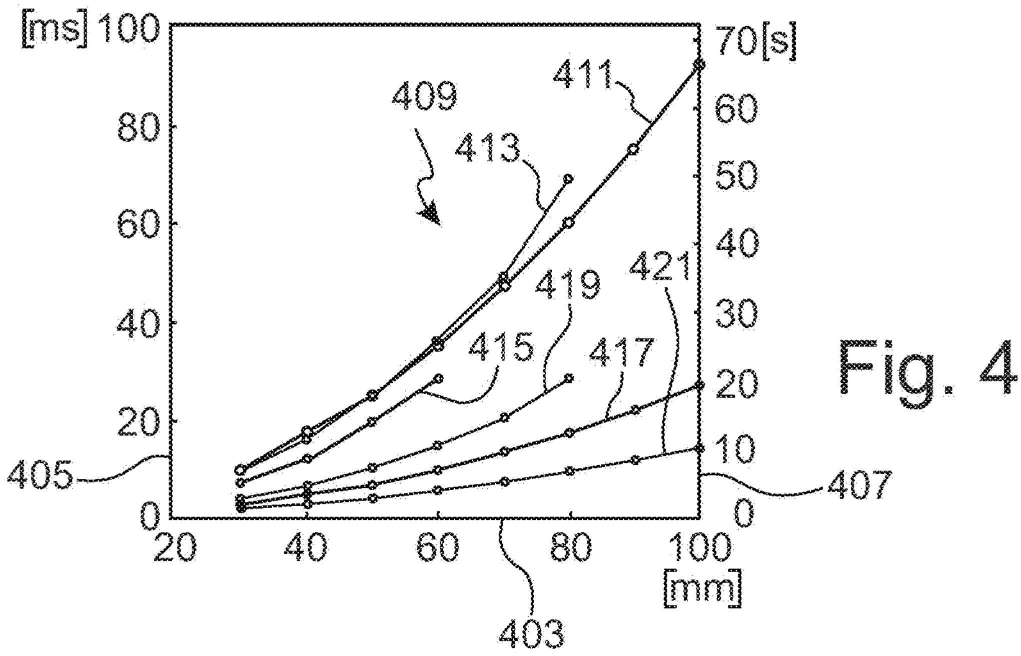
Figure 5:
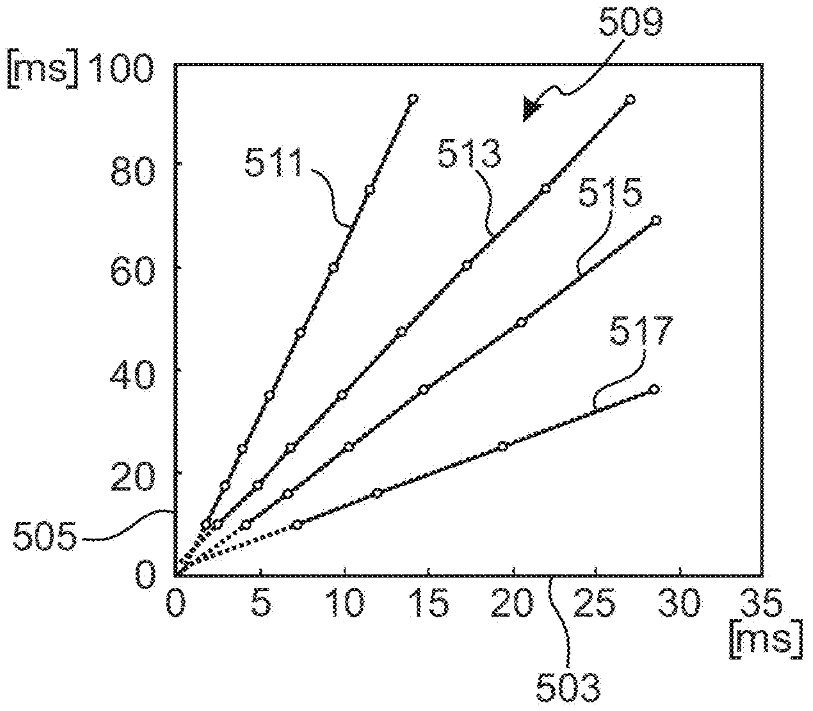
Figure 6:
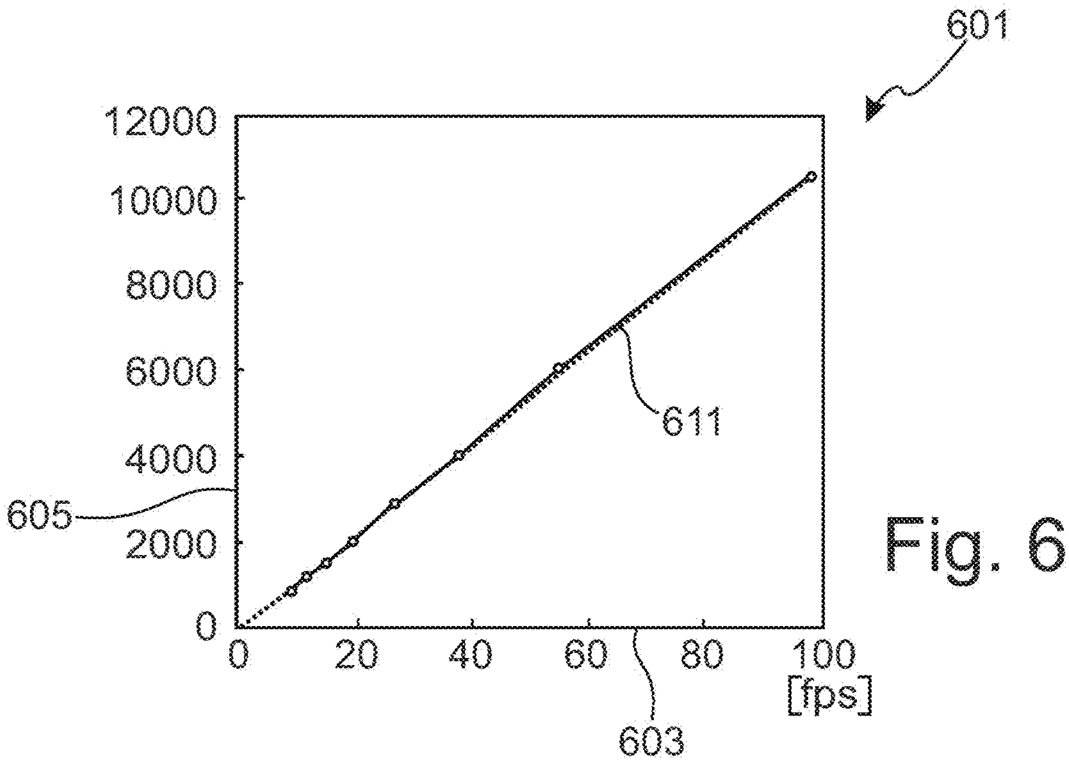
Figure 7:
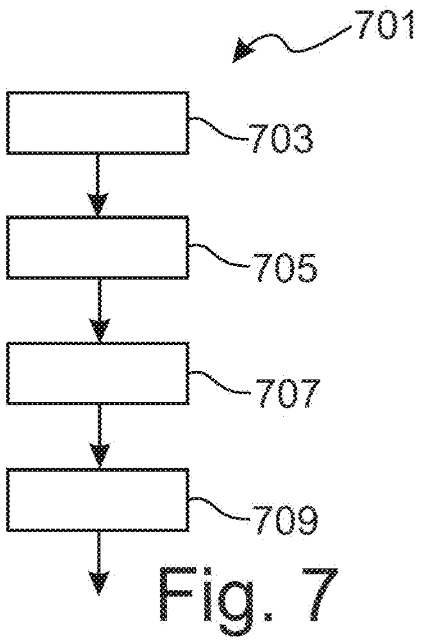
Figure 8:
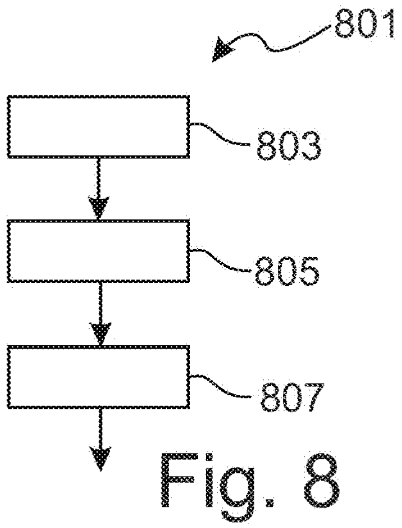
Figure 9:
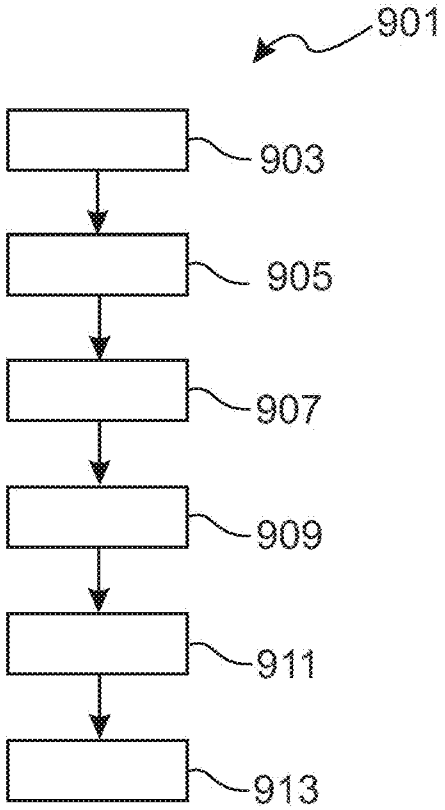

The invention is further explained on the basis of exemplary embodiments, in which is shown FIG. 1 a schematic representation of a laparoscopic system with a hyperspectral system in a side view, FIG. 2 a schematic representation of an alternative laparoscopic system with an alternative hyperspectral system, FIG. 3 a diagram for representing a respective signal-to-noise ratio in a spectral range being viewed for different measuring distances and exposure times, FIG. 4 a diagram for representing an exposure time of a hyperspectral sensor and a white light sensor at different measuring distances, FIG. 5 a diagram for representing a required exposure time of a hyperspectral sensor in dependence on the exposure times of a white light sensor, FIG. 6 a diagram for representing a motor speed in dependence on the refresh rate (FPS) used during a scanning process of a hyperspectral sensor, FIG. 7 a schematic flowchart of a method for calibrating and regulating a hyperspectral exposure duration, FIG. 8 a schematic flowchart of a method for regulating a motor speed of a hyperspectral sensor, and FIG. 9 a schematic flowchart of a method for automatically adjusting an exposure time.

A laparoscopic system 101 consists of a laparoscope 103 for viewing an abdominal cavity and a hyperspectral system 121 for evaluating corresponding image information of an object 191, represented as an example, in a viewing area 193. The laparoscope 103 has a shaft 111 represented as an example, which can be inserted into a trocar, for example, and guided into the abdominal cavity by means of the trocar. The shaft serves to direct light along an optical path 181 from the viewing area 193 to a lens adapter 117 on a side of the laparoscope 103 facing an operator. For example, a lens (not represented) can be applied to the lens adapter 117 such that the laparoscope 103 can be used as an optical aid without electronic aids and the lens serves to represent an image of the object 191 in the viewing area 193 to a viewer.

A connection 113 for a light channel 115 is provided on the shaft 111, with the light channel 115 being attached to the connection 113 laterally opposite the shaft 11. By means of the light channel 115, light from a light source, for example LED lighting, can be introduced into the shaft 111 such that the viewing area 193 and thus the object 191 can be illuminated by means of the light guided through the light channel 115 and the shaft 111.

In the present example, a hyperspectral system 121 is placed on the lens adapter 117 such that the light incident along the optical path 181 is guided into the hyperspectral system 121 through the lens adapter 117.

The hyperspectral system 121 has a housing 123 represented as an example, with all means for capturing corresponding images, in particular a colour image of the viewing area 193 and a hyperspectral image of the viewing area 193, being accommodated in the housing 123.

The light incident along the optical path 181 is split at a beam splitter 143 such that part of the incident light can be directed along an optical path 183 onto an image sensor 141. The image sensor 141 is here an RGB sensor and is therefore used to capture a colour image of the viewing area 193. For this purpose, the RGB sensor is equipped, for example, as a CMOS sensor with a Bayer filter.

The light partially emerging from the beam splitter 143 along an optical path 185 is directed through a high-pass filter glass 145 such that unwanted portions of the light directed from the viewing area 193 can be filtered out. The light is then directed along the optical path 185 through a lens 147 and then hits a transmission grating 149. By means of the transmission grating 149, the light is spectrally split and deflected and then directed by means of a lens 151 to an image sensor 142, which captures and processes correspondingly spectrally divided light information. The lens 147, the transmission grating 149, the lens 151 and the image sensor 142 are accommodated in a housing 124 within the housing 123 of the hyperspectral system 121. A so-called HSI system, i.e. a subsystem for hyperspectral observation, is accommodated within the housing 124.

A servomotor 161 is used here to mechanically adjust the arrangement of the lens 147, the transmission grating 149, the lens 151 and the image sensor 142 such that respectively one line of an image of the viewing area 193 can be imaged on the image sensor 142 and thus the spectral distribution of the incident light is imaged for this respective line. A so-called hyperspectral data cube is then generated from a large number of lines scanned in this way, i.e. multidimensional information about the spectral distribution of incident light from the viewing area 193.

A computer 125 is represented as an example, which captures and processes image information from the image sensor 141 via a data line 127 and image information from the image sensor 142 via a data line 131. Furthermore, the computer 125 can influence and control the servomotor 161 via a data line 129 such that the computer 125 can adjust and control the hyperspectral arrangement, i.e. the HSI system. For this purpose, the computer 125 captures, for example, exposure information of the image sensor 141 or an exposure distribution of the image sensor 141 and compares this with comparison information stored in the computer 125 or desired exposure information stored there. The computer 125 can then use the image data determined by means of the image sensor 141 to influence the servomotor 161 in such manner that, for example, a sampling rate, i.e. a respective sequence rate of the image lines, is adjusted in such manner that a respective image line with an optimal exposure time and thus with an optimal exposure can be captured. Furthermore, the computer 125 can control the image sensor 142 via the data line 131 and also read out corresponding image information, such that, for example, feedback of the captured image information of the image sensor 142 is used to check the change to the servomotor 161 carried out by the computer 125 and thus to determine the accuracy of the influence exerted.

Overall, it is possible to calibrate the HSI system by capturing the image information via the image sensor 141. In particular, this takes place directly during a respective capture, but can also be carried out step by step, for example for each line individually.

The computer 125 further carries out a calculation of how long a respective image capture of the object 191 is expected to last based on the exposure information captured with the image sensor 141 and reference information and empirical values stored as an example, and shows this information to a respective operator on an output device (not represented), such that this signals to the operator how long, for example, a position must be held securely and free of movement to capture an image. The successful capture of an image can then be acknowledged, for example, with a beep.

An alternative laparoscopic system 201 (represented in abstracted form) has an alternative hyperspectral system 221, which corresponds to the hyperspectral system 121 in its targeted effect, manages with an image sensor and without a beam splitter. The object 191 arranged in the viewing area 193 is viewed here analogously to the example described above; light falls along an optical path 281 into the hyperspectral system 221 (schematic representation). The light can then be directed via a pivotable mirror 231 to a mirror 241, a mirror 243 and to a further pivotable mirror 232, such that the light is first directed past the HSI system accommodated in the housing 223 via an optical path 285 to an image sensor 241. In this operating state, the image sensor 241 is able to generate a colour image of the object 191 and, for example, transmit it to a downstream computer.

In a second switching state, the light from the optical path 281 is directed along an optical path 283 through the HSI system in the housing 223 by disengaging the mirror 231 and the mirror 232 from the optical path 281. The mirrors 241 and 243 are thereby out of function and the optical path 285 is unused. The incident light then runs through the HSI system in the housing 223; a servomotor 261 is also represented as an example, which reproduces the function of the servomotor 161 in an analogue manner. Analogous to the previous example, a corresponding calibration of the image passing through the HSI system can then be carried out via a computer such that the image sensor 241 images an HSI image, in particular a respective line of an HSI image, in this switching state.

The representation with the mirrors 231 and 232 is chosen here as an example in order to illustrate the operating principle for the use of a single image sensor 241. The HSI system in the housing 223 can also be pivoted in and out of the optical path 281 or in another form each be directed along the optical path 283 or optionally along the optical path 285.

A diagram 301 represents a signal-to-noise ratio for different measuring distances, i.e. different distances, for example a tip of the shaft 111 to the object 191, and different exposure times, in the example shown with a so-called white reference, i.e. an object which has a uniform white colouring of known optical properties. An abscissa 303 of the diagram 301 shows corresponding wavelengths of incident light, an ordinate 305 shows a signal-to-noise ratio. Graphs 309 thus represent the dependence of the signal-to-noise ratio in relation to the light wavelength. This allows two effects to be shown, which are compensated for and achieved by the invention:

On the one hand, a function 311 with slight local deviations represents the signal-to-noise ratio for five different measuring distances and exposure times. Function 311 thus represents measuring at a distance of 25 mm with an exposure time of 2.6 ms, measuring at a measuring distance of 40 mm with an exposure time of 6.0 ms, and measuring at a measuring distance of 50 mm with an exposure time of 9.5 ms, measuring at a measuring distance of 75 mm with an exposure time of 20.0 ms and measuring at a measuring distance of 100 mm with an exposure time of 35.0 ms. This shows that sufficient exposure for a respective image sensor with a constant signal-to-noise ratio can be compensated for by respectively increasing the exposure time at an increased measuring distance.

Furthermore, functions 313, 315, 317 and 319 show a respective signal-to-noise ratio at different measuring distances, namely at 40 mm (function 313), 50 mm (function 315), 75 mm (function 317) and 100 mm (function 319). The exposure time is 2.6 ms in each case. This shows that the signal-to-noise ratio decreases steadily when the measuring distance is increased while maintaining an exposure time of 2.6 ms, which means that the quality of a possible image capture gradually decreases. A corresponding adjustment of an exposure time, for example, for the image sensor 142 by the computer 125 based on an exposure intensity determined by means of the image sensor 141 can therefore serve to carry out a calibration based on the effects shown in the diagram 301 in such a way that a successive adjustment of the exposure time with an increased measuring distance, for example is used to keep the image quality constant.

A diagram 401 shows a required exposure time of an overall HSI system consisting of an HSI system and an RGB sensor with increasing measuring distance and constant measured intensity for an exemplary wavelength of 610 nm on a white reference and a tissue phantom. This diagram 401 also represents automatically regulated exposure times of an RGB sensor when darkening and brightening. Such a tissue phantom is here an exemplary arrangement which approximately depicts the optical properties of a tissue located in the human body and is used for calibration or tests. A measuring distance is represented on an abscissa 403 of the diagram 401, and a first ordinate 405 represents the exposure time. A second ordinate 407 provides the necessary capture time for capturing 720 image lines.

Corresponding graphs 409 represent the respective functional connections.

A function 411 here shows the connection for an HSI capture when capturing a white reference. A function 413 shows a slightly increasing exposure time of the RGB sensor when the viewing area is darkened, a function 415 shows the opposite effect when the viewing area is brightened.

For capturing a tissue phantom, the function 417 shows the HSI capture of the tissue phantom, the function 419 shows corresponding effects on the RGB sensor to darken the viewing area and the function 421 shows the effects on the RGB sensor to brighten the viewing area.

A diagram 501 represents a corresponding correlation of a white light exposure time to an HSI exposure time, namely a corresponding correlation to an automatic regulation of corresponding exposure times of the colour image sensor with different illumination of the viewing area as well as exposure times of the HSI system dependent thereon for a constant intensity with 610 nm light wavelength selected as an example.

An abscissa 503 here represents the exposure time of the colour image sensor, an ordinate 505 represents the exposure time of the HSI sensor. Corresponding graphs 509 show the relationships:

A function 511 shows the corresponding relationship for darkening, a function 513 for brightening each on a white reference, for example a white object. A function 515 shows the relationship for darkening and a function 517 for brightening, each on a tissue phantom.

A diagram 601 shows a correlation of a necessary motor speed, for example the speed of the motor 161, in dependence on the set refresh rate (FPS) of the HSI system. An abscissa 603 here represents the refresh rate (FPS), an ordinate 605 represents a corresponding motor speed, which can be plotted, for example, as steps of a stepper motor or as a speed (in FIG. 6, for example, plotted as steps of a stepper motor). A function 611 here shows the corresponding relationship such that an exact image refresh rate of the HSI system can be controlled by means of a speed of the motor 161 controlled accordingly by, for example, the computer 125.

Corresponding methods for calibrating a medical imaging system, for example the laparoscopic system 101, are represented below:

A method 701 is used here to calibrate an HSI exposure duration:

First, an exposure time of the HSI sensor is set for a white balance at an optimal intensity and a smallest selected measuring distance. A white reference used for the white balance is then replaced 705 by a tissue phantom, with an intensity measured thereby serving as a reference for the further steps. Subsequently, the corresponding exposure times of the HSI sensor are varied 707 for different measuring distances, with this being carried out until the intensity measured in the corresponding previous step is reached as a reference. For all measuring distances determined in this way, an automatically regulated exposure time of the colour sensor is also determined when a corresponding viewing area is brightened and/or darkened. A functional relationship is then determined 709 between the exposure time of the colour sensor and the exposure time of the HSI sensor such that a calibration correlation is achieved and the system can be calibrated.

A method 801 shows regulating of an appropriate motor speed to influence an HSI system:

First, an HSI image of a square object, for example, is captured 803 at different image refresh rates of the HSI sensor. The motor speed is then adjusted 805 for the respective image refresh rates in such manner and until a respective ratio of the length of the viewed object to the width of the viewed object, which, as represented, is square, lies within a narrow tolerance around the value 1, for example between 0.94 and 1.06. For an ideally square object, this ratio would have to be 1 to achieve an optimal image refresh rate and true representation.

Finally, the functional relationship between the image refresh rate and the motor speed is determined 807, such that, for example, the correlation of the function 611 represented in the diagram 601 is determined and represented.

A method 901 represents the generation of an HSI capture with an automatically adjusted exposure time. First, a query 903 is made for a corresponding exposure time of the colour sensor, for example the RGB sensor 141. A resulting exposure time of the HSI sensor is then determined 905 using the functional relationships determined as described above.

As a result, a maximum possible image refresh rate is calculated 907 for a corresponding one while maintaining a corresponding exposure quality and image quality, with corresponding exposure times being able to be limited to a practical or technically feasible range.

As a result, a resulting motor speed is determined 909 based on the image refresh rate and based on the functional relationships shown, as represented above.

A capture time is then calculated 911 and displayed for a viewer or a user, with the basis for this calculation 911 depicting the number of images required in relation to the possible image refresh rate.

Finally, the required exposure times and image refresh rates of the HSI sensor as well as the motor speed are set 913 based on the previously generated calibration correlations.

LIST OF REFERENCE NUMERALS

101 Laparoscopic system
103 Laparoscope
111 Shaft
113 Connection
115 Light channel
117 Lens adapter
121 Hyperspectral system
123 Housing
124 Housing
125 Computer
127 Data line
129 Data line
131 Data line
141 Image sensor
142 Image sensor
143 Beam splitter
145 Filter glass
147 Lens
149 Transmission grating
151 Lens
161 Servomotor
181 Optical path
183 Optical path
185 Optical path
191 Object
193 Viewing area
201 Laparoscopic system
221 Hyperspectral system
223 Housing
231 Mirror
232 Mirror
241 Mirror
243 Mirror
261 Servomotor
281 Optical path
283 Optical path
285 Optical path
301 Diagram
303 Abscissa
305 Ordinate
309 Graphs
311 Function
313 Function
315 Function
317 Function
319 Function
401 Diagram

403 Abscissa
405 Ordinate
407 Ordinate
409 Graphs
411 Function
413 Function
415 Function
417 Function
419 Function
421 Function
501 Diagram
503 Abscissa
505 Ordinate
509 Graphs
511 Function
513 Function
515 Function
517 Function
601 Diagram
603 Abscissa
605 Ordinate
611 Function
701 Method
703 Setting
705 Replacing
707 Varying
709 Determining
801 Method
803 Capturing
805 Adjusting
807 Determining
901 Method
903 Querying
905 Determining
907 Calculating
909 Determining
911 Calculating
913 Setting

The invention claimed is:

1. A medical imaging device comprising:
a light source configured to illuminate a viewing area,
a lens having an optical path configured to capture the viewing area and to image first image information for a visible image of the viewing area on an image capturing device,
the image capturing device having a sensitivity distribution such that the first image information is captured by the image capturing device, wherein the imaging capturing device further images second image information for a spectral image of the viewing area such that the second image information is also captured by the image capturing device, and
an adjustment device configured to adjust image parameters of the image capturing device, wherein the adjustment device is associated with a control unit, wherein the first image information is captured by the control unit and the control unit controls the adjustment device in dependence on the first image information for adjusting the sensitivity distribution with a calibration correlation between the first image information and the second image information, wherein the adjustment device calibrates the second image information, based at least on the first image information, for the image capturing device.

2. The medical imaging device according to claim 1, wherein the adjustment device is introduced into the optical path by a switching device such that the first image information is captured by the control unit in a first switching state of the switching device, in which the adjustment device is not introduced into the optical path, and the control unit controls the adjustment device in a second switching state of the switching device based at least on the first image information for adjusting the sensitivity distribution with a calibration correlation between the first image information and the second image information, wherein the image capturing device has a first image sensor to capture the first image information and the second image information.

3. The medical imaging device according to claim 1, wherein the optical path has a first optical partial path configured to image the first image information on the image capturing device and a second optical partial path configured to image the second image information on the image capturing device, wherein the first image information is captured by the control unit in the first optical partial path and the control unit controls the adjustment device in the second optical partial path based at least on the first image information for adjusting the sensitivity distribution with a calibration correlation between the first image information and the second image information, wherein the image capturing device has a first image sensor associated with the first optical partial path with a first sensitivity distribution to capture the first image information and a second image sensor associated with the second optical partial path with a second sensitivity distribution to capture the second image information.

4. The medical imaging device according to claim 1, wherein the calibration correlation is formed based at least on one or more of: reference image information, and different reference image information with respective exposure settings.

5. The medical imaging device according to claim 1, wherein the calibration correlation is formed based at least on a white balance and/or based on a black balance, or
based on a plurality of white balances and/or based on a plurality of black balances, that are dependent on an exposure setting or dependent on a plurality of exposure settings of the image capturing device or the second image sensor.

6. The medical imaging device according to claim 1, wherein the calibration correlation is present for different illumination intensities of the light source.

7. The medical imaging device according to claim 1, wherein the adjustment device has a frame manipulator, wherein, the frame manipulator is configured to adjust a frame rate of the image capturing device, and/or a frame count of the image capturing device, the second image sensor, is configured to be adjusted and/or has an exposure manipulator, wherein, by the exposure manipulator, an exposure intensity and/or an exposure duration of the image capturing device, is adjusted.

8. The medical imaging device according to claim 1, wherein the image capturing device has a spectral sensor, or
a hyperspectral sensor with line-by-line scanning of image information of the viewing area, wherein the hyperspectral sensor has one or more of a slit aperture and a grating aperture for one or more of variable interruption and deflection of the respective image information.

9. The medical imaging device according to claim 8, wherein the adjustment device has a motor, wherein the slit aperture and/or the grating aperture is moved by the motor such that the variable interruption and/or deflection of the respective image information takes place by moving the slit aperture and/or grating aperture.

10. The medical imaging device according to claim 1, wherein the control unit is associated with a calculation unit configured to calculate a predicted capture duration of the respective image information based on the calibration correlation and/or based on operating parameters of the control unit, the image capturing device, the first image sensor and/or the second image sensor.

11. The medical imaging device according to claim 1, wherein the image capturing device has a sensor configured to capture an image visible to an operator, and/or the first image sensor has a sensor configured to capture an image visible to an operator, and wherein the first image sensor is an RGB sensor and/or a white light sensor.

12. A method to calibrate a medical imaging device comprising:

capturing the first image information of a visible image with an image capturing device such that the first image information is present in the image capturing device, controlling an adjustment device by a control unit by adjusting a second sensitivity distribution with a calibration correlation to calibrate the second image sensor based on second image information for a spectral image of the viewing area such that calibrated second image information from the second image sensor is obtained.

13. The method according to claim 12, wherein the control is carried out based on partial information of the first image information including an average pixel intensity of the first image information, based on a maximum pixel intensity of the first image information and/or based on a pixel intensity distribution of the first image information.

14. The method according to claim 12, wherein the second image sensor is controlled line by line such that the calibration is carried out line by line for a respective line.

15. The method according to claim 12, wherein a control measurement is carried out with a comparison of the sensitivity distribution, the calibration correlation, the first sensitivity distribution and/or the second sensitivity distribution to check the accuracy of the calibration by a control unit associated with the adjustment device.

16. The method according to claim 12, wherein the calibration correlation is converted based on a ratio of a first image size of the first image information and a second image size of the second image information, in particular based on a respective length and/or based on a respective width of the respective image information, such that a size-adjusted, format-adjusted, length-adjusted and/or width-adjusted overlay of the calibration correlation with the respective sensitivity distribution is possible.

17. The method according to claim 12, wherein the calibration is carried out during the capture of the first image information by an ongoing calibration and/or after the capture of the first image information by a subsequent calibration.

18. The method according to claim 12, wherein the illumination intensity of the light source is adjusted in dependence on the calibration correlation.

* * * * *